United States Patent
Ortiz (10) Patent No.: US 7,635,373 B2
(45) Date of Patent: Dec. 22, 2009

(54) ABSORBABLE GASTRIC RESTRICTION DEVICES AND METHODS

(75) Inventor: Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 388 days.

(21) Appl. No.: 11/420,368

(22) Filed: May 25, 2006

(65) Prior Publication Data

US 2007/0276411 A1    Nov. 29, 2007

(51) Int. Cl.
*A61B 17/10*    (2006.01)
(52) U.S. Cl. ................... 606/142; 623/23.72; 227/178.1
(58) Field of Classification Search ............ 623/23.72; 606/142, 143; 227/178.1, 175.1, 19
See application file for complete search history.

(56) References Cited

U.S. PATENT DOCUMENTS

| | | |
|---|---|---|
| 2,004,013 A | 6/1935 | Reed |
| 2,004,014 A | 6/1935 | Sanford |
| 2,004,172 A | 6/1935 | Niday |
| 4,841,888 A | 6/1989 | Mills et al. |
| 5,041,129 A | 8/1991 | Hayhurst et al. |
| 5,080,663 A | 1/1992 | Mills et al. |
| 5,217,486 A | 6/1993 | Rice et al. |
| 5,269,809 A | 12/1993 | Hayhurst et al. |
| 5,376,101 A | 12/1994 | Green et al. |
| 5,398,670 A | 3/1995 | Ortiz et al. |
| 5,437,681 A | 8/1995 | Meade et al. |
| 5,462,558 A | 10/1995 | Kolesa et al. |
| 5,514,159 A | 5/1996 | Matula et al. |
| 5,540,705 A | 7/1996 | Meade et al. |
| 5,571,119 A | 11/1996 | Atala |
| 5,584,861 A | 12/1996 | Swain et al. |
| 5,709,693 A | 1/1998 | Taylor |
| 5,713,910 A | 2/1998 | Gordon et al. |
| 5,755,730 A | 5/1998 | Swain et al. |
| 5,814,071 A | 9/1998 | McDevitt et al. |
| 5,860,992 A | 1/1999 | Daniel et al. |

(Continued)

FOREIGN PATENT DOCUMENTS

WO    WO-95/19140    7/1995

(Continued)

OTHER PUBLICATIONS

U.S. Appl. No. 10/729,622, filed Feb. 2004, Deem et al.*

*Primary Examiner*—(Jackie) Tan-Uyen T. Ho
*Assistant Examiner*—Christina Lauer
(74) *Attorney, Agent, or Firm*—Nutter McClennen & Fish LLP (57) ABSTRACT

Disclosed herein are endoscopic gastric restriction devices and methods. In one embodiment, the device generally includes a shaft having an end effector on a distal end thereof. The end effector includes several elongate segments that are coupled to one another and include opposed troughs formed therein. Each trough is configured to suction and pull tissue into the trough, as well as hold a fastener that can be delivered to tissue disposed within the trough. As a result, the end effector can deliver multiple fasteners to opposed walls of tissue. As the fasteners are delivered into tissue, the segments can be detached from the device, so that the end effector remains in the tissue. Over time, the end effector can be absorbed and/or dissolve, leaving the fasteners behind.

18 Claims, 9 Drawing Sheets

U.S. PATENT DOCUMENTS

| | | | |
|---|---|---|---|
| 5,887,594 A | 3/1999 | LoCicero, III | |
| 5,899,921 A | 5/1999 | Caspari et al. | |
| 5,902,321 A | 5/1999 | Caspari et al. | |
| 6,010,515 A | 1/2000 | Swain et al. | |
| 6,036,694 A | 3/2000 | Goble et al. | |
| 6,200,329 B1 | 3/2001 | Fung et al. | |
| 6,346,111 B1 | 2/2002 | Gordon et al. | |
| 6,358,259 B1 | 3/2002 | Swain et al. | |
| 6,443,962 B1 | 9/2002 | Gaber | |
| 6,454,778 B2 | 9/2002 | Kortenbach | |
| 6,494,888 B1 | 12/2002 | Laufer et al. | |
| 6,500,195 B2 | 12/2002 | Bonutti | |
| 6,506,196 B1 | 1/2003 | Laufer | |
| 6,524,328 B2 | 2/2003 | Levinson | |
| 6,540,789 B1 | 4/2003 | Silverman et al. | |
| 6,558,400 B2 | 5/2003 | Deem et al. | |
| 6,572,629 B2 | 6/2003 | Kalloo et al. | |
| 6,663,639 B1 | 12/2003 | Laufer et al. | |
| 6,719,763 B2 | 4/2004 | Chung et al. | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,858 B2 | 11/2004 | Namatame et al. | |
| 6,835,200 B2 | 12/2004 | Laufer et al. | |
| 6,869,395 B2 | 3/2005 | Page et al. | |
| 6,908,427 B2 | 6/2005 | Fleener et al. | |
| 6,955,643 B2 | 10/2005 | Gellman et al. | |
| 7,399,304 B2 * | 7/2008 | Gambale et al. | 606/139 |
| 2001/0023352 A1 | 9/2001 | Gordon et al. | |
| 2002/0107530 A1 | 8/2002 | Sauer et al. | |
| 2002/0193809 A1 | 12/2002 | Meade et al. | |
| 2003/0032967 A1 | 2/2003 | Park et al. | |
| 2003/0083674 A1 | 5/2003 | Gibbens | |
| 2003/0109900 A1 | 6/2003 | Martinek | |
| 2003/0120265 A1 | 6/2003 | Deem et al. | |
| 2003/0120272 A1 | 6/2003 | Schneider et al. | |
| 2003/0120292 A1 | 6/2003 | Park et al. | |
| 2003/0171760 A1 | 9/2003 | Gambale | |
| 2003/0181924 A1 | 9/2003 | Yamamoto et al. | |
| 2003/0208209 A1 * | 11/2003 | Gambale et al. | 606/144 |
| 2003/0225312 A1 | 12/2003 | Suzuki et al. | |
| 2003/0229296 A1 | 12/2003 | Ishikawa et al. | |
| 2003/0233104 A1 | 12/2003 | Gellman et al. | |
| 2003/0233108 A1 | 12/2003 | Gellman et al. | |
| 2004/0002720 A1 | 1/2004 | Kortenbach et al. | |
| 2004/0006351 A1 | 1/2004 | Gannoe et al. | |
| 2004/0024386 A1 | 2/2004 | Deem et al. | |
| 2004/0034369 A1 | 2/2004 | Sauer et al. | |
| 2004/0059350 A1 | 3/2004 | Gordon et al. | |
| 2004/0082963 A1 | 4/2004 | Gannoe et al. | |
| 2004/0098050 A1 | 5/2004 | Foerster et al. | |
| 2004/0122452 A1 | 6/2004 | Deem et al. | |
| 2004/0122453 A1 * | 6/2004 | Deem et al. | 606/151 |
| 2004/0122473 A1 | 6/2004 | Ewers et al. | |
| 2004/0147958 A1 | 7/2004 | Lam et al. | |
| 2004/0162568 A1 | 8/2004 | Saadat et al. | |
| 2004/0193184 A1 | 9/2004 | Laufer et al. | |
| 2004/0194790 A1 | 10/2004 | Laufer et al. | |
| 2004/0210243 A1 | 10/2004 | Gannoe et al. | |
| 2004/0215058 A1 | 10/2004 | Zirps et al. | |
| 2004/0225305 A1 | 11/2004 | Ewers et al. | |
| 2005/0015101 A1 | 1/2005 | Gibbens et al. | |
| 2005/0033319 A1 | 2/2005 | Gambale et al. | |
| 2005/0055038 A1 | 3/2005 | Kelleher et al. | |
| 2005/0070921 A1 | 3/2005 | Ortiz et al. | |
| 2005/0070926 A1 | 3/2005 | Ortiz | |
| 2005/0070931 A1 | 3/2005 | Li et al. | |
| 2005/0070934 A1 | 3/2005 | Tanaka et al. | |
| 2005/0070935 A1 | 3/2005 | Ortiz | |
| 2005/0075653 A1 | 4/2005 | Saadat et al. | |
| 2005/0075654 A1 | 4/2005 | Kelleher | |
| 2005/0143760 A1 | 6/2005 | Imran | |
| 2005/0143762 A1 | 6/2005 | Paraschac et al. | |
| 2005/0149067 A1 | 7/2005 | Takemoto et al. | |
| 2005/0165419 A1 | 7/2005 | Sauer et al. | |
| 2005/0177176 A1 | 8/2005 | Gerbi et al. | |
| 2005/0192599 A1 | 9/2005 | Demarais | |
| 2005/0192601 A1 | 9/2005 | Demarais | |
| 2005/0203488 A1 | 9/2005 | Michlitsch et al. | |

FOREIGN PATENT DOCUMENTS

| | | |
|---|---|---|
| WO | WO-00/61012 | 10/2000 |
| WO | WO-01/10312 | 2/2001 |
| WO | WO-01/66001 | 9/2001 |
| WO | WO-01/89393 | 11/2001 |
| WO | WO-02/096327 | 12/2002 |
| WO | WO-2004/021894 | 3/2004 |
| WO | WO-2005/034729 | 4/2005 |

* cited by examiner

ABSORBABLE GASTRIC RESTRICTION DEVICES AND METHODS

FIELD OF THE INVENTION

The present invention relates to surgical devices and methods for attaching tissue, for example during a gastric restriction procedure.

BACKGROUND OF THE INVENTION

Morbid obesity is a serious medical condition that has become highly pervasive in the United States as well as other countries, and the trend appears to be heading in a negative direction. Complications associated with morbid obesity include hypertension, diabetes, coronary artery disease, stroke, congestive heart failure, multiple orthopedic problems, and pulmonary insufficiency with markedly decreased life expectancy. The monetary and physical costs associated with morbid obesity are substantial. In fact, it is estimated that the costs relating to obesity are in excess of 100 billion dollars in the United States alone.

A variety of surgical procedures have been developed to treat obesity, the most common of which is a Roux-en-Y gastric bypass (RYGB). While this procedure is highly complex, it is commonly utilized to treat people exhibiting morbid obesity. Other forms of bariatric surgery include the Fobi pouch, bilio-pancreatic diversion, and gastroplastic or "stomach stapling." In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secrete stomach juices flowing through the intestinal track. A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch and the attached segment of duodenum are then reconnected to form another anastomotic connection to the Roux loop at a location approximately 50 to 150 cm from the stoma, typically using a stapling instrument. It is at this connection that the digestive juices from the bypass, stomach, pancreas, and liver enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, post-operative recovery time can be quite lengthy and painful. In view of the highly invasive nature of the current RYGB procedure, other less invasive procedures have been developed. One such procedure is a gastric restriction, which involves the application of vertical staples along the stomach to create an appropriate pouch. This procedure is commonly performed laparoscopically and, as such, requires substantial preoperative, operative, and postoperative resources.

With the foregoing in mind, procedures that allow for the performance of gastric reduction surgery in a time efficient and patient friendly manner are needed. Accordingly, the present invention provides devices and methods for performing a gastric restriction.

SUMMARY OF THE INVENTION

The present invention provides various devices and methods for attaching opposed tissue surfaces to one another during a variety of surgical procedures, such as a gastric restriction. In one embodiment, a gastric restriction device is provided that includes a shaft having an end effector removably coupled to a distal end thereof. The end effector includes a plurality of segments that are releasably coupled to the end effector, and anterior and posterior troughs extending therethrough and configured to receive tissue therein. In use, the end effector is adapted to receive a plurality of fasteners therein and to apply the fasteners to engage tissue disposed within each trough to mate the tissue in the anterior trough to the tissue in the posterior trough.

The device can include various features for firing one or more fasteners, but in one exemplary embodiment the device includes at least one firing bar that extends through the end effector for releasing a plurality of fasteners that are disposed in the end effector to allow the fasteners to penetrate and engage tissue disposed within the troughs. For example, where each fastener includes an anterior portion adapted to engage tissue in the anterior trough and a posterior portion adapted to engage tissue in the posterior trough, the end effector can include a first firing bar that is adapted to release the anterior portion of the fasteners and a second firing bar that is adapted to release the posterior portion of the fasteners. In use, the firing bar can be slidably removed from the plurality of segments to release the plurality of segments from the end effector, as well as to release the plurality of fasteners disposed in the end effector to allow the fasteners to engage tissue disposed within the anterior and posterior troughs.

In another embodiment, the device can include a plurality of suction ports formed within each trough for suctioning tissue therein. For example, a plurality of suctions ports can be formed in the anterior trough for suctioning an anterior tissue surface into the anterior trough, and a plurality of suction ports can be formed in the posterior trough for suctioning a posterior tissue surface into the posterior trough. The end effector can also include a first suction tube configured to apply suction through the suction ports formed in the anterior trough, and a second suction tube configured to apply suction through the suction ports formed in the posterior trough.

The fasteners used with the end effector can also have a variety of configurations, but in an exemplary embodiment each fastener can include an anterior portion that is positioned to engage tissue disposed within the anterior trough and a posterior portion that is positioned to engage tissue disposed within the posterior trough. The anterior and posterior portions of each fastener can be, for example, substantially C-shaped with opposed legs that are adapted to penetrate and engage tissue, and the anterior and posterior portions can be mated to one another.

The device can also include a variety of other features, such as an articulation mechanism that can movably couple the end effector to the shaft to move the end effector from a first insertion position where it is substantially aligned with the shaft, to a second actuation position where it is positioned at an angle relative to a longitudinal axis of the shaft. The end effector can also include a tapered distal tip to facilitate insertion into a lumen. In an exemplary embodiment, the distal tip can be releaseable and it can be formed from an absorbable material.

Methods for fastening tissue are also disclosed herein. In one aspect, a method for fastening tissue can include positioning an end effector between anterior and posterior tissues and delivering a plurality of fasteners disposed within the end effector to cause each fastener to engage the anterior and posterior tissues. The method can also include releasing at least a portion of the end effector that contains the fasteners from the end effector. In one embodiment, the end effector can include a plurality of segments and each segment can have a fastener disposed therein. The device can also include at least one firing bar that extends through the end effector and that is slidably removable from the end effector to release the segments from the end effector and to fire the fasteners. In an exemplary embodiment, the device includes first and second firing bars, and the fasteners can be delivered to the tissue by slidably removing the first firing bar from the end effector to release an anterior portion of each fastener, and simultaneously or subsequently slidably removing the second firing bar from the end effector to release a posterior portion of each fastener. As a result, the anterior portion of each fastener can engage the anterior tissue, and the posterior portion of each fastener can engage the posterior tissue.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for attaching opposed tissue surfaces to one another. In one embodiment, a gastric restriction device is provided and it is configured to be inserted translumenally into the stomach to allow opposed walls of the stomach to be pulled together, thereby creating a small pouch within the stomach which reduces the rate of gastric emptying. The device includes an end effector that is configured to apply one or more fasteners to opposed walls of the stomach to thereby attach the opposed walls to one another. In particular, each fastener can be configured to engage both the anterior tissue wall and the posterior tissue wall of the stomach. Once the tissues are attached, a portion of the end effector, with the fasteners disposed therein, can be released from the device and they can remain in the stomach. Eventually, the end effector and/or fasteners can be dissolved or absorbed as food. This is particularly advantageous in that it eliminates the need for suturing the fasteners to attach the opposed tissue surfaces to one another. A person skilled in the art will appreciate that the devices and methods disclosed herein are not limited to use in performing a gastric restriction, and may be applied in various soft tissue apposition procedures where tissue is drawn together either permanently or temporarily. A person skilled in the art will further appreciate that the present invention has applications in conventional endoscopic and open surgical instrumentation, as well applications in robotic-assisted surgery.

Figure 1A:
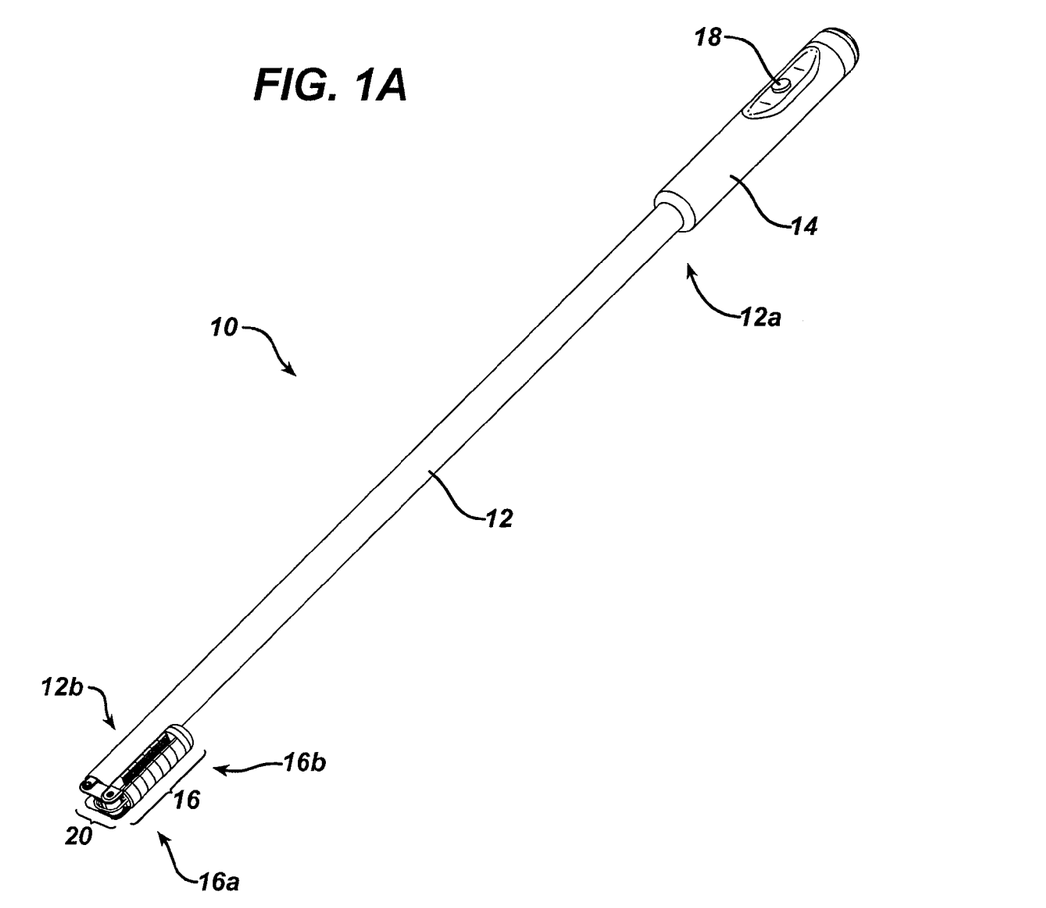
FIG. 1A is perspective view of one embodiment of a gastric restriction device in an articulated position.

FIG. 1A illustrates one exemplary embodiment of a gastric restriction device 10. As shown, the device 10 generally includes a shaft 12 having a proximal end 12a with a handle 14 coupled thereto or formed thereon, and a distal end 12b that is coupled to an end effector 16. The end effector 16 includes several segments 22a-22f that are removably coupled to one another, and opposed anterior and posterior troughs 24, 25 that extend through each segment 22a-22f along a length of the end effector 16. Each trough 24, 25 is configured to receive tissue therein. The segments 22a-22f are also adapted to hold fasteners that are configured to engage tissue disposed within the anterior and posterior troughs 24, 25. In use, as the fasteners are delivered into tissue, the segments 22a-22f can be detached from the end effector 16 so that they remain in the tissue. Over time, the segments 22a-22f can be absorbed and/or dissolve, leaving the fasteners behind.

The shaft 12 of the device 10 can have a variety of configurations, but it is preferably adapted to be laparoscopically or endoscopically inserted to a surgical site. For example, the shaft 12 can have a substantially cylindrical elongate configuration and it can be substantially flexible to allow it to be introduced translumenally, e.g., through the esophagus. As indicated above, the distal end 12b of the shaft 12 is coupled to the end effector 16. While various mating techniques can be used, in one embodiment, the shaft 12 and the end effector 16 can be configured to articulate relative to one another. FIG. 1C illustrates the device 10 in the insertion position, in which the shaft 12 and the end effector 16 are substantially linearly aligned. Following the placement of the device 10 within tissue, the end effector 16 can be articulated from the insertion position to an actuation position, as shown in FIG. 1B, in which the end effector 16 is positioned at an angle relative to the shaft 12.

Figure 1B:
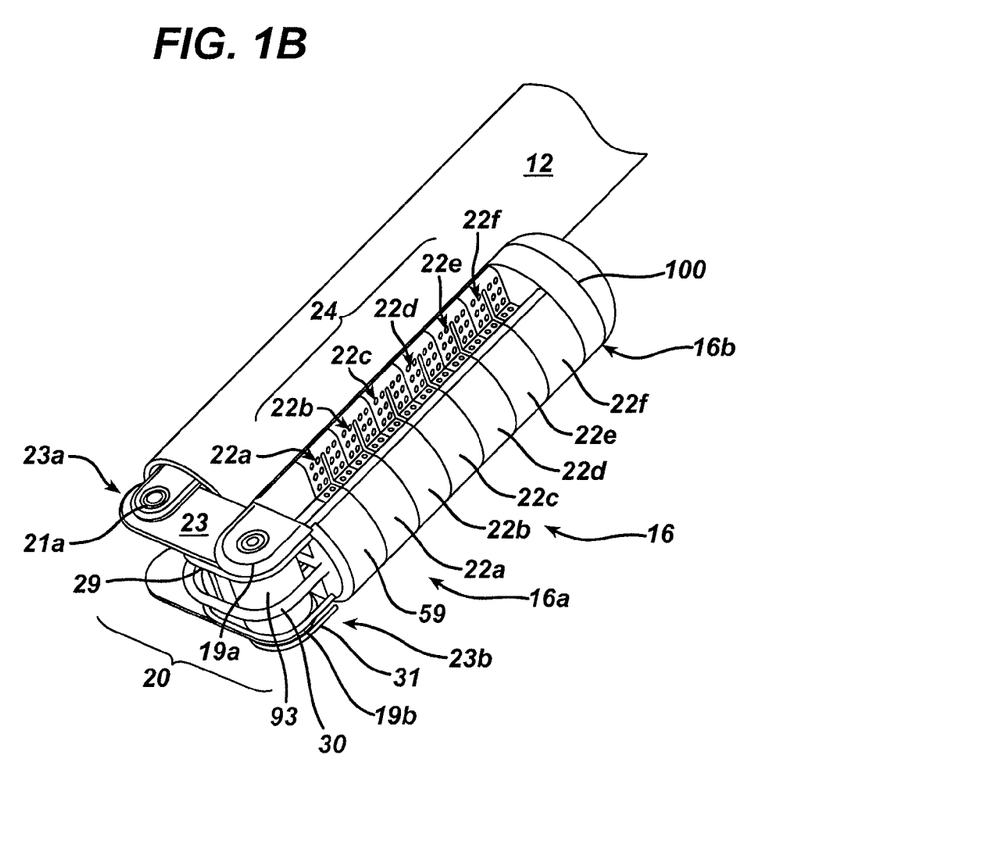
FIG. 1B is an enlarged perspective view of a distal end of the device of FIG. 1A, shown in an articulated position.
Figure 1C:
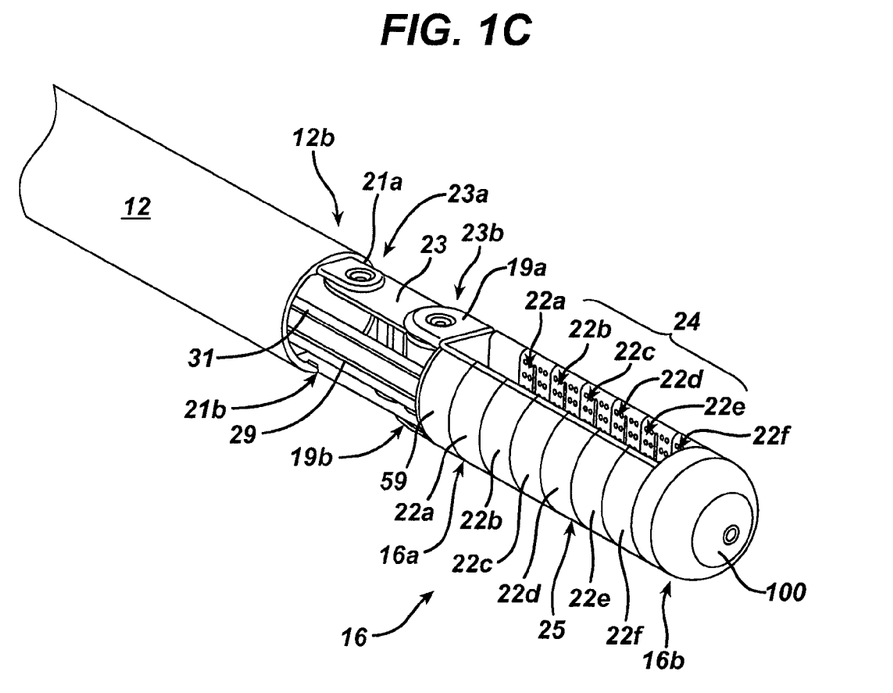
FIG. 1C is a perspective view of the distal end of the device of FIG. 1A, shown in an insertion position.
Figure 5:
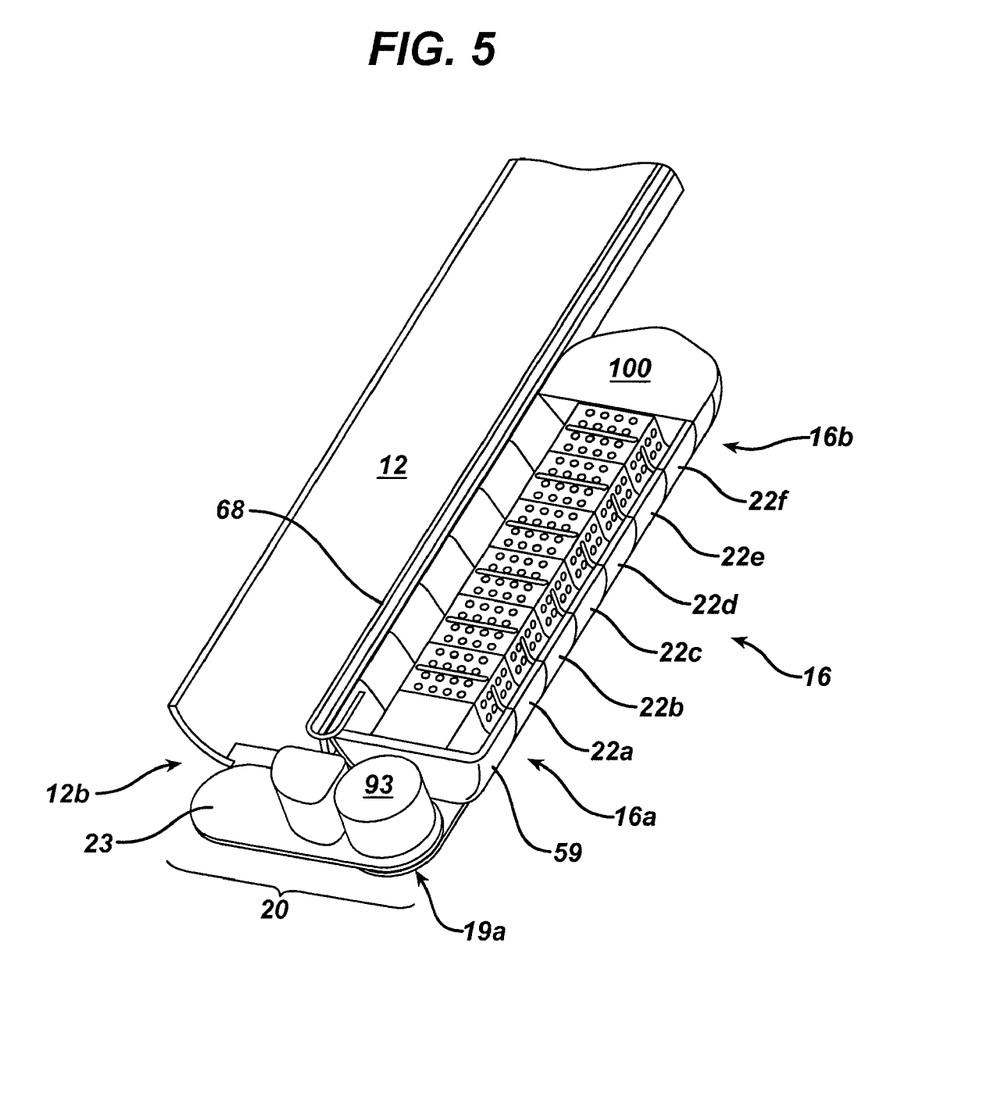
FIG. 5 is a cross-sectional view of a distal end of the device of FIGS. 1A-1C.

A variety of techniques can be used to articulate the end effector 16 relative to the shaft 12, but in one exemplary embodiment the end effector 16 can be coupled to the distal end 12b of the shaft 12 by a pivot portion 20, as shown in FIGS. 1B and 1C. The pivot portion 20 can include a linkage 23 having a first end 23a that is pivotally coupled to opposed arms 21a, 21b formed on the distal end 12b of the shaft 12, and a second end 23b that is pivotally coupled to opposed arms 19a, 19b formed on a connector 59 of the end effector 16, as will be discussed below. The second end 23b of the linkage 23 can also include a roller 93 rotatably disposed therein and adapted to facilitate actuation of the device 10, as will also be discussed below. The device 10 can also include one or more cables for articulating the end effector 16. FIG. 5 illustrates a single cable 68 that extends from the proximal end 12a of the shaft 12, through the shaft 12, along a side of the linkage 23, and connects to a connector 59 on the end effector 16. In use, tension can be applied to the cable 68 to pull the connector 59 towards the distal end 12b of the shaft 12, causing the end effector 16 to be positioned at an angle relative to the shaft 12. In other embodiments the device can include two or more cables to allow for multi-directional movement of the end effector. While the exemplary embodiment illustrates a pivot portion 20, a person having ordinary skill in the art will appreciate that a variety of other techniques can be used to effect movement of the device from the insertion position to the actuation position. For example, the end effector 16 itself can be configured to flex along its longitudinal axis. Alternatively, the end effector 16 can be fixedly coupled to or integrally formed with the distal end 12b of the shaft 12.

The shaft 12 can also include a handle 14 located on the proximal end 12a thereof to facilitate manipulation and handling of the device 10. While the handle 14 can have any configuration that allows a user to conveniently hold and operate the device 10, as shown in FIG. 1A the handle 14 has a substantially elongate shape. The handle 14 can include features to facilitate articulation and/or actuation of the device 10. For example, FIG. 1A illustrates a sliding actuator lever 18 that can be coupled to the cable 68 and that allows tension to be selectively applied thereto. In alternate embodiments, rotatable knobs or dials can be used to selectively apply tension to the cable. A locking mechanism (not shown) can also be associated with the sliding actuator lever to hold the cable in position once tension is applied. While not shown, the handle 14 can also include openings from which a first and second firing bar 29, 31 can extend. In use, the firing bars 29, 31 can be manually pulled in a proximal direction to remove the firing bars 29, 31 from the end effector, thus delivering the fasteners 60 to tissue and releasing the segments 22a-22f from the end effector 16, as will be discussed in more detail below. In other embodiments, the handle can include a slidable lever, or rotatable dial or knob to effect the actuation of the firing bars. The handle 14 can also include other features, such as a port for delivering suction to the end effector 16, as will be discussed in more detail below.

The end effector 16 is shown in more detail in FIGS. 1B-1C. While the configuration of the end effector 16 can vary, it is preferably adapted to be introduced translumenally, e.g., through a natural orifice such as the esophagus. In the illustrated embodiment, the end effector 16 has a generally elongate cylindrical shape and includes a proximal end 16a that can have a connector 59 formed thereon for coupling to the shaft 12, and a distal end 16b that can have a blunt, pointed, and/or tapered distal tip 100 that is configured to facilitate the insertion of the device 10 into tissue. The end effector 16 can also include a plurality of segments 22a-22f that are coupled to one another. As shown in FIGS. 1B and 1C, the segments 22a-22f are disposed between the connector 59 and the tip 100 of the end effector 16. In use, the segments 22a-22f, as well as the distal tip 100, are configured to be released from the end effector 16, and in particular from the connector 59, as will be discussed in more detail below.

Figure 2:
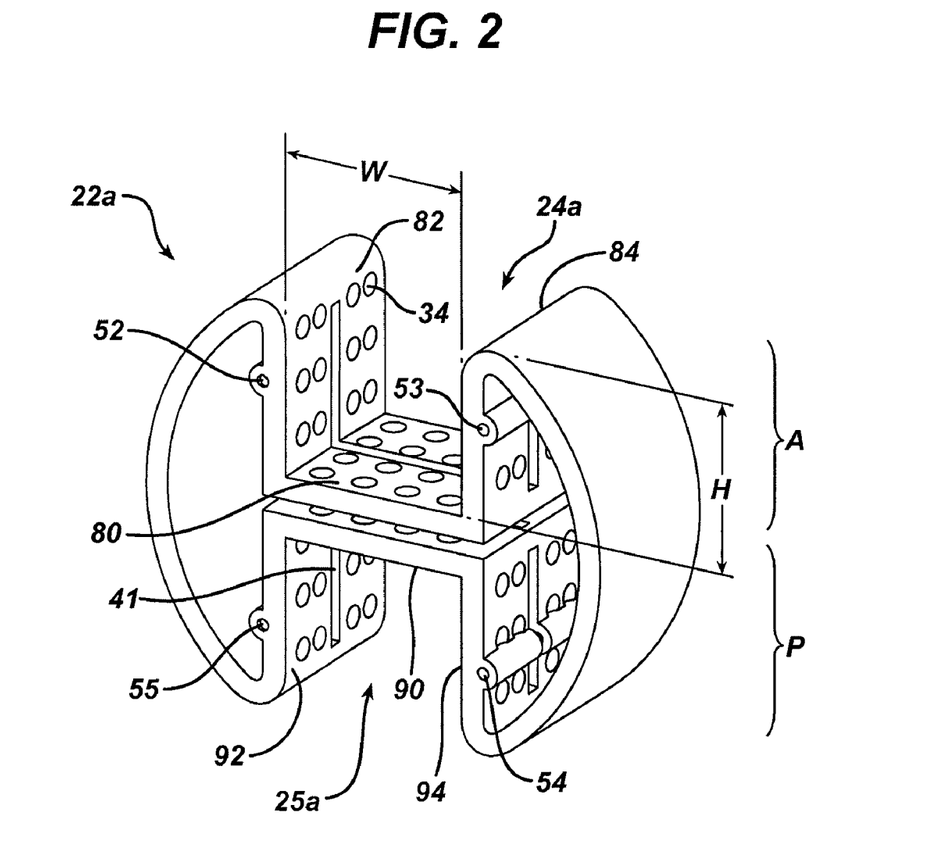
FIG. 2 is a perspective view of a segment of the device of FIGS. 1A-1C.

While the configuration of each segment 22a-22f can vary depending upon the type of fasteners used, FIG. 2 illustrates one exemplary segment 22a. As shown, the segment 22a is substantially H-shaped with anterior and posterior portions A, P having opposed anterior and posterior troughs 24a, 25a formed therein. The anterior and posterior troughs 24a, 25a can have any shape and size, but they are preferably adapted to receive a sufficient amount of tissue therein such that the tissue can be engaged by a fastener, as will be discussed in more detail below. As shown in FIG. 2, the anterior and posterior troughs 24a, 25a are both substantially square or rectangular, and have opposed sidewalls 82, 84, 92, 94 and a base wall 80, 90 extending between the sidewalls 82, 84, 92, 94. The opposed sidewalls 82, 84, 92, 94 can also have thru-holes 52, 53, 54, 55 formed therein for receiving one more fastener-retaining members or firing bars that are used to hold fasteners within the trough and to mate the segments 22a-22f to the end effector 16, as will be discussed below. In use, when the segments 22a-22f are mated to form the end effector 16, the troughs 24a-24f, 25a-25f in each segment 22a-22f align to form opposed anterior and posterior troughs 24, 25 extending along a length of the end effector 16 between the proximal and distal ends 16a, 16b thereof.

As explained above, each trough 24a, 25a is configured to receive tissue therein. While a variety of techniques can be used to position tissue within the troughs 24a, 25a, in one embodiment each trough 24a, 25a can include a plurality of suction ports 34 formed therein for suctioning tissue into the trough 24a, 24b. The number of suction ports 34 can vary, and each suction port 34 can have any shape and size, such as circular or elongate slots. The suction ports 34 can also be formed at various locations within the troughs 24a, 25a, but as shown in FIG. 2, each trough 24a, 25a includes a plurality of suction ports 34 formed in the base wall 80, 90 and the opposed sidewalls 82, 84, 92, 94 thereof. The suction ports 34 can also be positioned in any pattern that is effective for engaging tissue, such as in equally spaced rows within the troughs 24a, 25a. In use, one or more suction tubes (tube 30 is shown in FIG. 1B) can extend through each segment 22a-22f and can be used to apply suction to an interior of the segments 22a-22f, thereby generating a suction force within the troughs 24a, 25a for drawing tissue therein. For example, FIG. 2 illustrates segment 22a having a generally hollow configuration. First and second suction tubes (not shown) can extend through the elongate shaft 12 and through the hollow interior of the segment 22a. The hollow interior portion of the segment 22a can also optionally be separated into zones or regions, to allow suction to be selectively applied to only a portion of one or both troughs 24a, 25a. For example, the anterior portion A of the segment 22a can have a first interior cavity with a suction tube extending therethrough, and the posterior portion P of the segment 22a can have a second interior cavity with a suction tube extending therethrough. In use, suction can be applied to the first interior cavity to suction tissue into the anterior trough 24a, and suction can subsequently be applied to the second interior cavity to suction tissue into the posterior trough 25a. A person skilled in the art will appreciate that various suction zones can be formed to allow for differential suction. The suction force can be generated using a pump or other element coupled to a proximal end of each suction tube at the proximal end 12a of the shaft 12 or the handle 14 of the device 10 to pull air into the ports and suction the tissue therein.

Once tissue is suctioned or otherwise positioned within each trough 24a-24f, 25a-25f, the end effector 16 can be adapted to deliver one or more fasteners to the tissue disposed within the troughs 24a-24f, 25a-25f. While a variety of techniques can be used to retain the fasteners in the end effector 16, in one embodiment, each segment 22a-22f can include one or more channels formed therein for seating a fastener. The number and location of the channels can vary depending upon the desired amount of tissue to be cinched, however in the exemplary embodiment each segment 22a-22f is configured to retain a single fastener. Thus, referring to FIG. 2, the segment 22a can include a first channel 40 formed in the anterior trough 24a and extending through the base wall 80 and the opposed sidewalls 82, 84 thereof, and a second channel 41 formed in the posterior trough 25a and extending through the base wall 90 and the opposed sidewalls 92, 94 thereof. The channels 40, 41 can extend transverse to a longitudinal axis of the end effector 16 to allow the fasteners to extend across the troughs 24a, 25a and thereby engage tissue disposed therein, as will be discussed in more detail below.

Figure 3A:
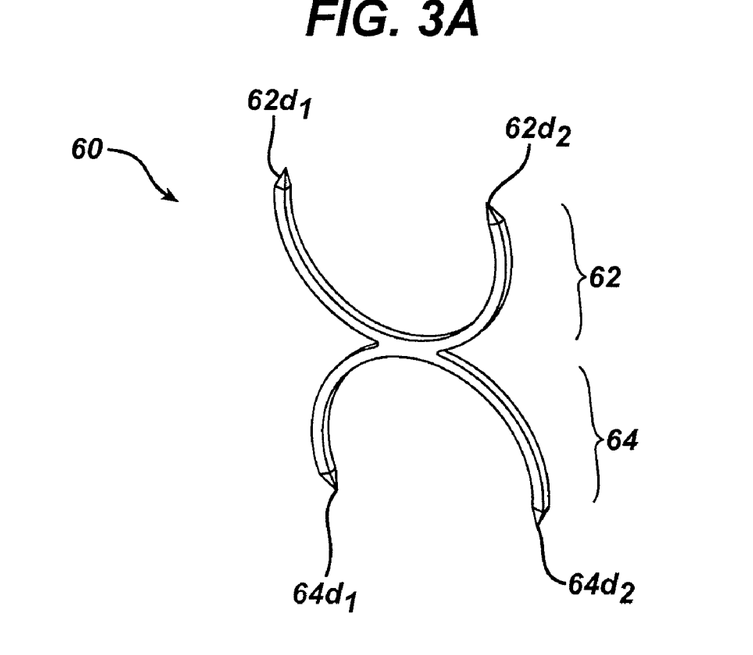
FIG. 3A is a perspective view of one embodiment of a fastener in an open position for use with the device of FIGS. 1A-1C.
Figure 3B:
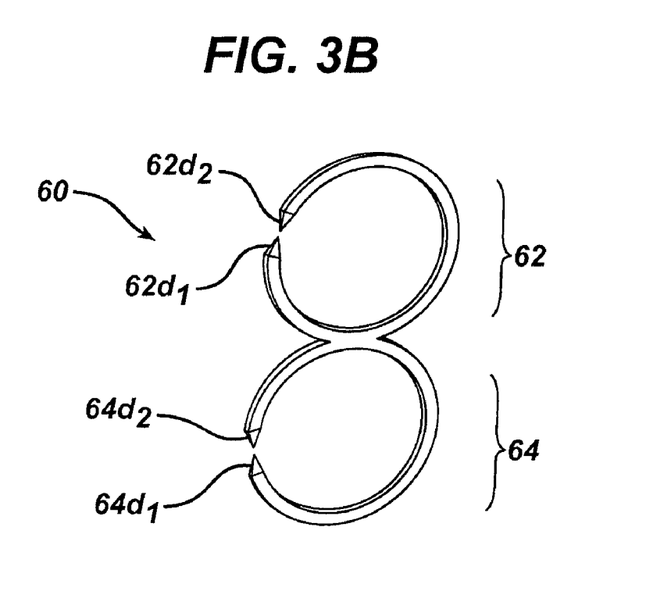
FIG. 3B is a perspective view of the fastener of FIG. 3A in a closed position.

A person skilled in the art will appreciate that the shape and size of the channels 40, 41 can vary depending upon the type of fasteners used, and various fasteners known in the art can be used. In one exemplary embodiment, as shown in FIGS. 3A and 3B, the fasteners 60 can have anterior and posterior portions 62, 64 that are mated together. The anterior and posterior portions 62, 64 can each be in the form of a clip having opposed first and second legs $62d_1$, $62d_2$, $64d_1$, $64d_2$ that are adapted to penetrate tissue. While the opposed legs $62d_1$, $62d_2$, $64d_1$, $64d_2$ can have the same shape and size, in an exemplary embodiment, as shown, one of the legs on each portion 62, 64, e.g., legs $62d_2$, $64d_2$, can be longer than the other leg on each portion 62, 64, e.g., legs $62d_1$, $64d_1$. This will allow the longer legs $62d_2$, $64d_2$ to be released to extend toward the shorter legs $62d_1$, $64d_1$ and thereby close the fastener without the need to release the shorter legs $62d_1$, $64d_1$, as will be discussed in more detail below. FIG. 3A illustrates the fastener 60 in an open position, in which the legs $62d_1$, $62d_2$, $64d_1$, $64d_2$ are substantially C-shaped, and FIG. 3B illustrates the fastener 60 in a closed position, in which the legs $62d_1$, $62d_2$, $64d_1$, $64d_2$ come together to form a ring-shaped member. In an exemplary embodiment, the fastener 60 is biased to the closed position shown in FIG. 3B to allow the fasteners to be self-deployed when the legs $62d_1$, $62d_2$, $64d_1$, $64d_2$ are released. The fasteners 60 can also include features to facilitate penetration of tissue, such as pointed legs and/or lubrication. FIGS. 3A-3B illustrate fastener 60 having pointed legs $62d_1$, $62d_2$, $64d_1$, $64d_2$. A person skilled in the art will appreciate that the fasteners 60 can be formed from a variety of biocompatible and superelastic materials, including, by way of non-limiting example, shape memory metals such as nitinol. Various techniques can also be used to manufacture the fasteners. For example, the fastener 60 shown in FIGS. 3A and 3B can be manufactured using a wire cutting or stamping process on a nitinol sheet.

Figure 4A:
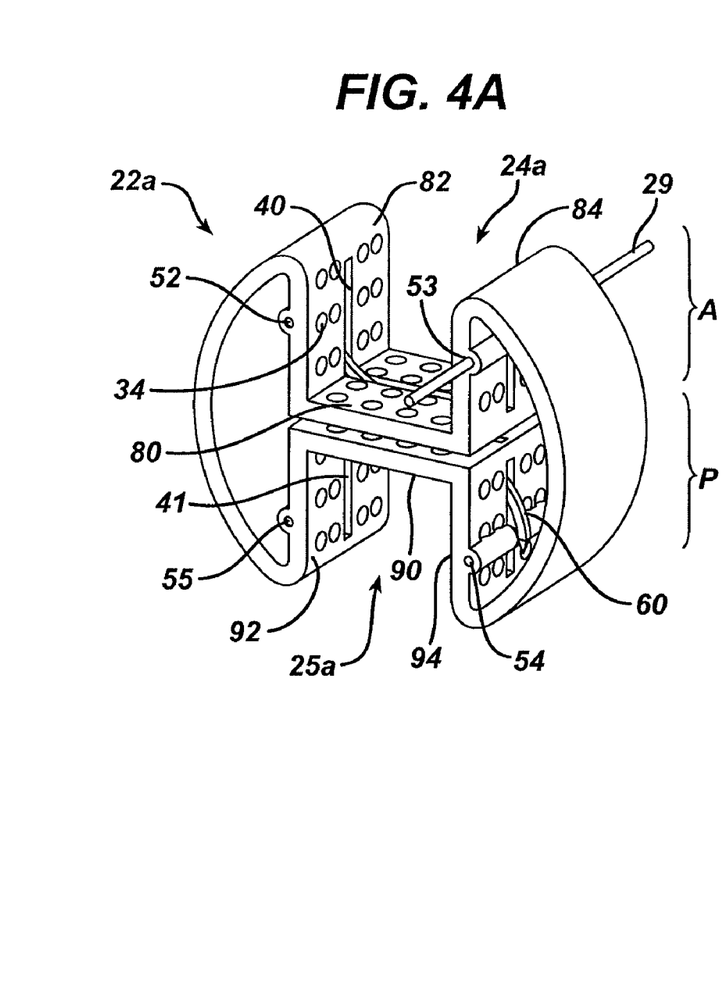
FIG. 4A is a perspective view of the segment of FIG. 2 with a fastener disposed therein.
Figure 4B:
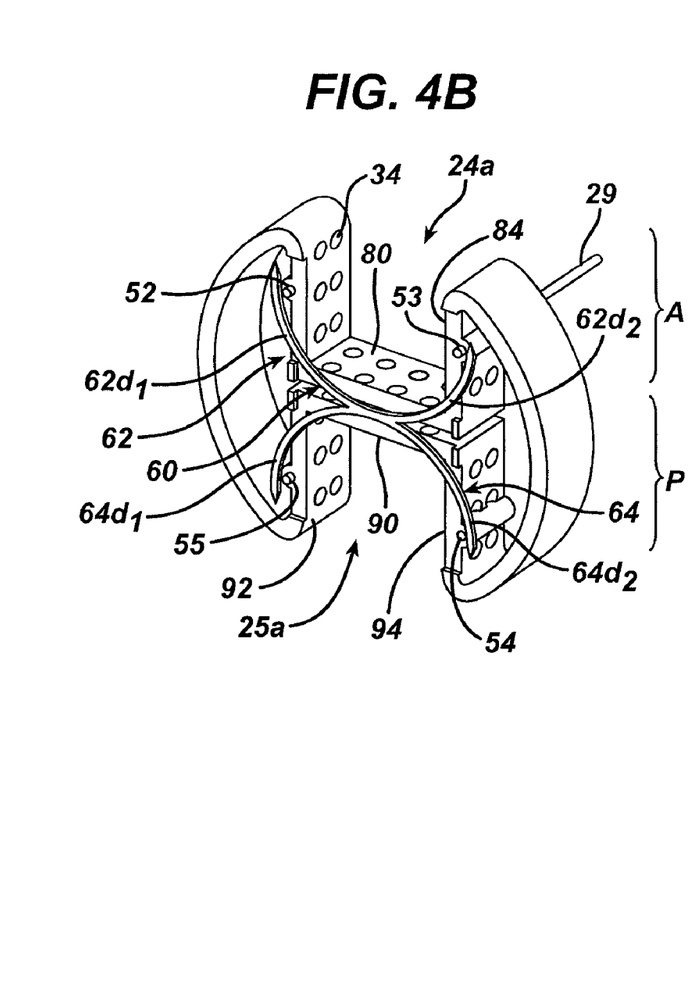
FIG. 4B is a cross-sectional view of the segment of FIG. 4A.

FIGS. 4A-4B illustrate a fastener 60 disposed within a segment, e.g., segment 22a. As shown, the anterior and posterior portions 62, 64 of the fastener 60 are disposed within the channels 40, 41 such that the legs $62d_1$, $62d_2$, $64d_1$, $64d_2$ of the anterior and posterior portions 62, 64 of the fastener 60 are positioned on opposed sides of the troughs 24a, 25a, while the mid-portion of the fastener 60 is held between the base walls 80, 90 of the segment 22a. The opposed legs $62d_1$, $62d_2$, $64d_1$, $64d_2$ of the fasteners 60 can be held within the channels 40, 41 in an open configuration using one or more fastener-retaining members or firing bars, as will be discussed below. Upon release from the channels 40, 41, the fasteners 60 can close to form a ring-shaped or substantially oblong-shaped member that engages the tissue in the troughs 24a, 25a.

As indicated above, the legs $62d_1$, $62d_2$, $64d_1$, $64d_2$ of the fasteners 60 can be releasably retained within the channels 40, 41 using various techniques, but in an exemplary embodiment they are retained within the channels 40, 41 using one or more fastener-retaining members or firing bars that can extend through the segments 22a-22f. The number of fastener-retaining members or firing bars can vary depending upon the configuration of the fasteners, but in an exemplary embodiment the device 10 includes anterior and posterior firing bars 29, 31 that extend through the thru-holes 53, 54 on a first side of the anterior and posterior regions A, P of the segments 22a-22f, and anterior and posterior fastener-retaining members (not shown) that extend through the thru-holes 52, 55 on the opposed sides of the anterior and posterior regions A, P of the segments 22a-22f. The fastener-retaining members retain a first leg of the fasteners 60 within one side of the segment, and the firing bars retain the opposed leg within the opposed side of the segment, thereby holding the fasteners 60 in an open position. In use, the fastener-retaining members can remain within the segments 22a-22f to mate the segments 22a-22f, while the firing bars 29, 31 can be slidably removed to release the fasteners 60, segments 22a-22f, and the distal tip 100 from the end effector 16. Thus, the fastener-retaining members can extend along the length of the segments 22a-22f, between the proximal-most segment 22a and the distal-most segment 22f or the distal tip 100, and the anterior and posterior firing bars 29, 31 can extend through the entire end effector 16, around the roller 93 and linkage 23, and through the shaft 12. The firing bars 29, 31 can be releasably retained within the last segment 22f or the distal tip 100 using, for example, a friction fit. In use, the roller 93 allows the firing bars 29, 31 to extend therearound when the device 10 is articulated, thus facilitating the removal of the firing bars 29, 31 from the device 10. When the firing bars 29, 31 are slidably removed, one leg on each of the anterior or posterior portions of the fasteners 60 is released into tissue. The leg will thus extend across the trough, through tissue disposed within the trough, and will move to the closed configuration in which the terminal end of the leg is adjacent to or in contact with the opposed leg. When the firing bars are removed, the segments 22a-22f are also released from the end effector 16 such that they are left behind in the tissue engaged by the fasteners 60. The fastener-retaining members will remain in the segments to hold the segments together. While the exemplary embodiment illustrates the use of two firing bars and two fastener-retaining members, one skilled in the art will appreciate that the device can include any number or firing bars and/or fastener-retaining members. For example, the device could include four firing bars, all of which are removable to release all four legs of each fastener.

One skilled in the art will appreciate that the firing bars and the cable can be made of a variety of materials, however in an exemplary embodiment the firing bars are made of a material that has a flexibility that is greater than a flexibility of the material used to form the cable so as to prevent the firing bars from interfering with the articulation force of the cable during removal of the firing bars. Exemplary materials for the firing bars can include, by way of non-limiting example, a shape memory material, such as nitinol, that is frozen using liquid carbon dioxide to maintain its shape, titanium, or stainless steel. Exemplary materials for the cable can include, by way of non-limiting example, titanium or stainless steel.

Figure 6A:
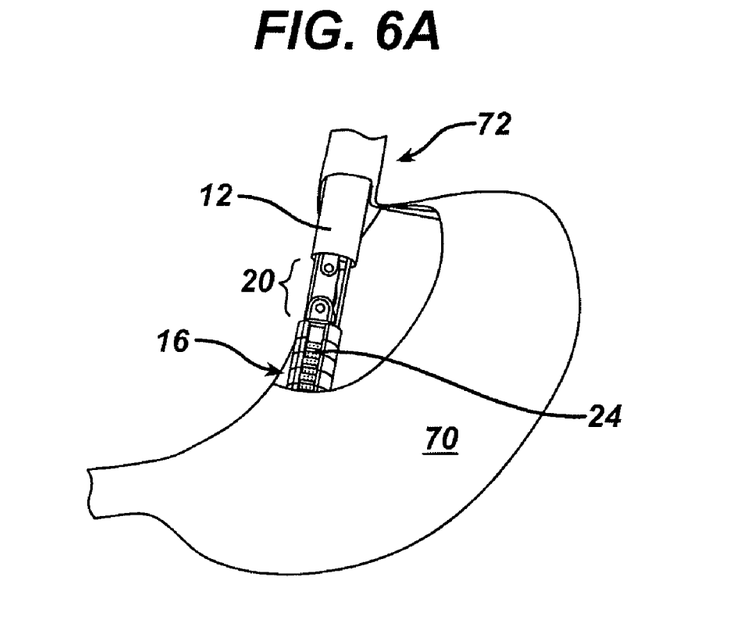
FIG. 6A is a partially cut-away perspective view of the device of FIGS. 1A-1C upon insertion into a stomach.
Figure 6B:
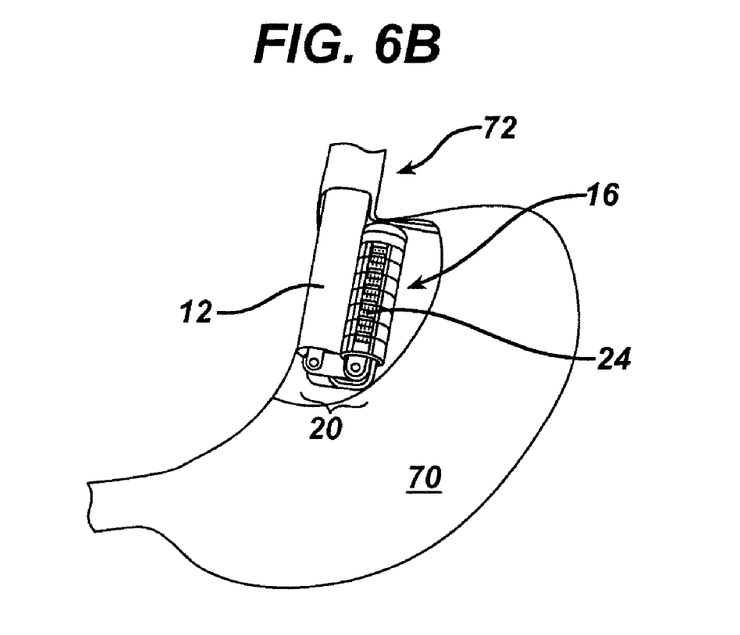
FIG. 6B is a partially cut-away perspective view of the device and stomach of FIG. 6A following articulation of the end effector to position the end effector adjacent to tissue to be fastened.

The present invention also provides methods for attaching opposed tissue surfaces, for example, to perform a gastric restriction. While the method is described in connection with device 10, a person skilled in the art will appreciate that various other devices can be used. Following preparation of the patient as known in the art, the device 10 can be inserted into a natural or created orifice to position the device 10 at a target site. As shown in FIG. 6A, the device 10 is introduced translumenally through the esophagus 72 to position the end effector 16 within the stomach 70. The device 10 is preferably inserted in the insertion position where the shaft 12 and the end effector 16 are longitudinally aligned. An endoscope disposed around or mounted directly on the device 10 can optionally be used to facilitate positioning of the end effector 16. Once the device 10 is positioned at the target site, the lever 18 on the handle 14 can be moved to apply tension to the articulation cable 68. This causes the end effector 16 to pivot about the pivot portion 20 relative to the shaft 12, such that it is positioned at an angle relative to the shaft 12, as shown in FIG. 6B. The cable 68 can then optionally be locked in position using a locking mechanism to maintain the position of the end effector 16 relative to the shaft 12.

Once the end effector 16 is positioned at a target site, suction can be applied to the end effector 16 via the suction ports to cause the tissue 70 to be suctioned into the troughs 24, 25. As shown, the opposed walls of the stomach 70 that are to be attached to one another to create the restriction are suctioned into the troughs 24, 25. In one embodiment, where the tissues to be suctioned are spaced a distance apart from one another, suction can be applied to one of the troughs, e.g., the anterior trough, to cause tissue positioned on an anterior side of the device to be received therein. The device can then be moved towards the second tissue, and suction can be applied to the second trough, e.g., the posterior trough, to cause the posterior tissue to be received therein.

After tissue is received within the troughs 24, 25 the fasteners 60 can be applied to the tissue 70. In an exemplary embodiment, the firing bar 29 located on one side, e.g., the anterior side of the end effector 16, can be actuated by pulling the bar in a proximal direction to remove it from the end effector 16. As a result, a first leg of the anterior portion of each fastener 60 will be sequentially released, starting with the leg of the distal-most fastener. The leg will move to the closed position, extending through tissue held within the anterior trough 24. Simultaneously or subsequently, the firing bar 31 located on the posterior side of the end effector 16 can be actuated by pulling the bar 31 in a proximal direction to remove it from the end effector 16. Removal of the firing bar 31 will cause the leg of the posterior portion of each fastener 60 to be sequentially released, allowing the leg to move to the closed position, and thus penetrate the tissue disposed within the posterior trough 25. When the firing bars 29, 31 are removed from the end effector 16 the segments 22a-22f will be released from the end effector 16 and disposed within tissue engaged by the fasteners 60. If the tip 100 is not connected to the segments 22a-22f, removal of the firing bars 29, 31 will also release the tip 100 such that it is free to separate from the segments 22a-22f. In an exemplary embodiment, the distal tip 100 of the end effector 16 is formed from a dissolvable material, such as a sugar gelatin, to allow the tip 100 to dissolve and pass through the body. In alternate embodiments, where the device has four firing bars, the four firing bars can be simultaneously or subsequently actuated to effect the release of the fasteners into tissue.

Once the firing bars 29, 31 are removed, the locking mechanism can optionally be unlocked and the tension on the cable 68 relieved by releasing the actuator lever 18 on the handle. As a result, when the device 10 is moved proximally out of the lumen, the shape of the lumen causes the device 10 to straighten such that proximal end 16a of the end effector returns to the insertion position and the connector 59 is aligned with the shaft 12. The shaft 12 can then be removed from the body, leaving the segments 22a-22f and the fasteners 60 within the tissue 70. In an exemplary embodiment, the segments 22a-22f can be formed from a bioabsorbable or dissolvable material, such as polyglycolic acid (PGA) or polydioxanone (PDS), to allow the segments 22a-22f to become absorbed as food, while the fasteners 60 remain in the tissue.

Figure 6C:
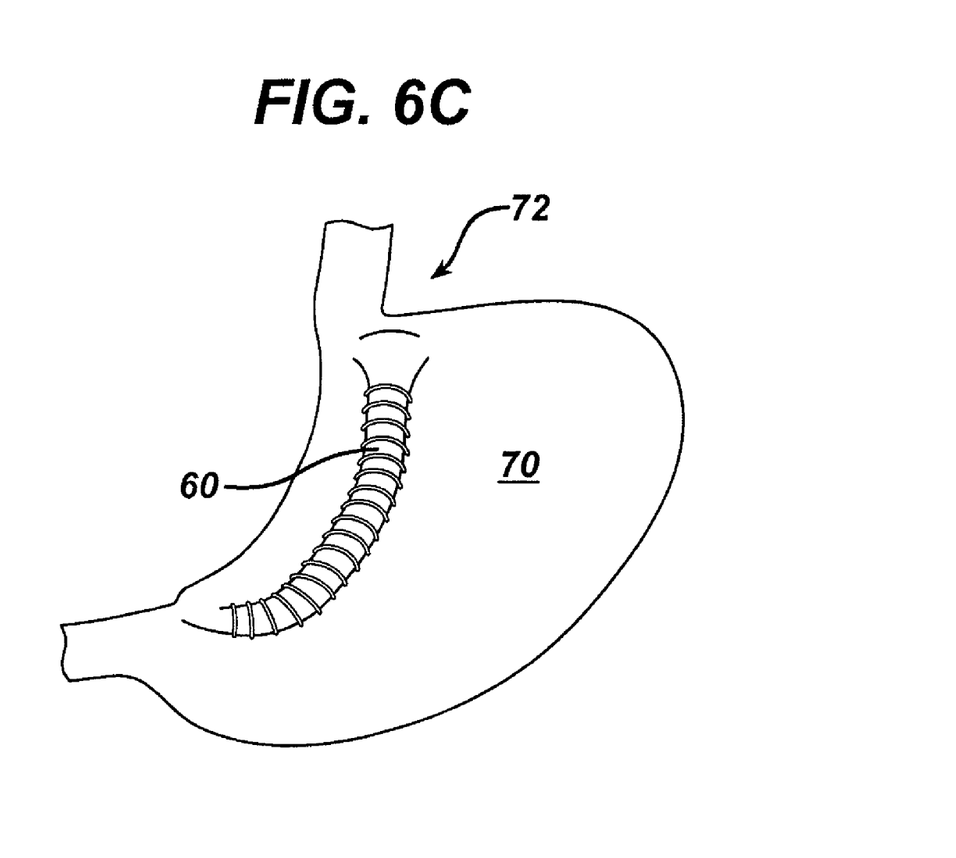
FIG. 6C is a perspective view of the stomach of FIG. 6B following removal of the device, and showing the fasteners applied to the stomach to reduce the size thereof.

The resulting structure of the stomach 70 is that of a small tubular pouch, as shown in FIG. 6C. The pouch may extend the full length between the esophagus 72 and the pylorus or it may extend only a portion of the distance from the esophagus 72 to the pylorus. Regardless of the length, the gastric remnant allows gastric acid to pass into the food stream, while the small stomach pouch creates a reduced passageway that restricts the passage of food therethrough. This is particularly advantageous in that it eliminates the need for sutures to connect the fasteners.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device (such as the end effector) can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An endoscopic gastric restriction device, comprising:
a shaft having an end effector removably coupled to a distal end thereof and including a plurality of segments releasably coupled to one another, the plurality of segments including anterior and posterior troughs extending through the segments and configured to receive tissue therein;
a plurality of fasteners disposed within the end effector and adapted to engage tissue disposed within the anterior and posterior troughs;
at least one firing bar extending through the end effector, each firing bar being configured to release the plurality of segments from the end effector and to release the plurality of fasteners disposed in the end effector to allow the fasteners to penetrate and engage tissue disposed within the troughs.

2. The device of claim 1, wherein each fastener includes an anterior portion positioned to engage tissue disposed within the anterior trough and a posterior portion positioned to engage tissue disposed within the posterior trough.

3. The device of claim 2, wherein the anterior portion of each fastener is substantially C-shaped with opposed legs adapted to penetrate and engage tissue, and the posterior portion of each fastener is substantially C-shaped with opposed legs adapted to penetrate and engage tissue, the anterior and posterior portions being mated to one another.

4. The device of claim 1, wherein each fastener includes an anterior portion adapted to engage tissue in the anterior trough, and a posterior portion adapted to engage tissue in the posterior trough, and wherein the end effector includes a first firing bar adapted to release the anterior portion of the fasteners and a second firing bar adapted to release the posterior portion of the fasteners.

5. The device of claim 1, further comprising an articulation mechanism that movably couples the end effector to the shaft and is adapted to move the end effector from a first insertion position where it is substantially aligned with the shaft to a second actuation position where it is positioned at an angle relative to a longitudinal axis of the shaft.

6. An endoscopic gastric restriction device, comprising:
a shaft having an end effector removably coupled to a distal end thereof and including a plurality of segments releasably coupled to one another, the plurality of segments including anterior and posterior troughs extending through the segments and configured to receive tissue therein; and
a plurality of fasteners disposed within the end effector and adapted to engage tissue disposed within the anterior and posterior troughs;
wherein the plurality of segments are formed from an absorbable material.

7. The device of claim 1, wherein each trough includes a plurality of suction ports formed therein for suctioning tissue into the trough.

8. An endoscopic gastric restriction device, comprising an end effector having an elongate configuration with a plurality of segments releasably coupled to one another, the plurality of segments including opposed anterior and posterior troughs formed therein for receiving tissue; and
a plurality of fasteners disposed within the plurality of segments, each fastener including an anterior clip having first and second legs configured to engage tissue disposed within the anterior trough and a posterior clip mated to the anterior clip and having first and second legs configured to engage tissue disposed within the posterior trough to thereby mate the tissues.

9. The device of claim 8, wherein each segment includes one of the plurality of fasteners disposed therein.

10. The device of claim 8, wherein the plurality of segments are releasably mated by at least one firing bar extending therethrough.

11. The device of claim 10, wherein the at least one firing bar is adapted to be slidably removed from the plurality of segments to thereby release and separate the plurality of segments from the end effector.

12. The device of claim 10, wherein the at least one firing bar is adapted to release the plurality of fasteners disposed in the end effector to allow the fastener to engage tissue disposed within the anterior and posterior troughs.

13. The device of claim 8, further comprising a first firing bar removably disposed though the end effector and adapted to release one of the first and second legs of the anterior clip, and a second firing bar removably disposed though the end effector and adapted to release one of the first and second legs of the posterior clip.

14. The device of claim 8, wherein the end effector is movably coupled to a distal end of an elongate insertion shaft configured to be introduced translumenally.

15. The device of claim 8, further comprising a plurality of suction ports formed within each trough for suctioning tissue therein.

16. The device of claim 8, wherein the end effector includes a first suction tube configured to apply suction through a plurality of suction ports formed in first sidewall of the trough, and a second suction tube configured to apply suction through a plurality of suctions ports formed in a second opposed sidewall of the trough.

17. The device of claim 8, wherein the plurality of segments are formed from an absorbable material.

18. The device of claim 8, wherein the end effector includes a tapered distal tip to facilitate insertion into a lumen, the distal tip being formed of an absorbable material.

* * * * *

UNITED STATES PATENT AND TRADEMARK OFFICE
CERTIFICATE OF CORRECTION

PATENT NO.        : 7,635,373 B2                                      Page 1 of 1
APPLICATION NO. : 11/420368
DATED             : December 22, 2009
INVENTOR(S)       : Mark S. Ortiz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 599 days.

Signed and Sealed this

Twenty-first Day of December, 2010

David J. Kappos
*Director of the United States Patent and Trademark Office*